US010416265B2

(12) United States Patent
Sanchez Gonzalez et al.

(10) Patent No.: US 10,416,265 B2
(45) Date of Patent: Sep. 17, 2019

(54) METHOD AND SYSTEM FOR GENERATING MR IMAGES OF A MOVING OBJECT IN ITS ENVIRONMENT

(71) Applicants: KONINKLIJKE PHILIPS N.V., Eindhoven (NL); CENTRO NACIONAL DE INVESTIGACIONES CARDIOVASCULARES CARLOS III (CNIC), Madrid (ES)

(72) Inventors: Javier Sanchez Gonzalez, Eindhoven (NL); Nils Dennis Nothnagel, Eindhoven (NL); Borja Ibanez Cabeza, Eindhoven (NL); Rodrigo Fernandez Jimenez, Eindhoven (NL); Valentin Fuster Carulla, Eindhoven (NL)

(73) Assignees: KONINKLIJKE PHILIPS N.V., Eindhoven (NL); CENTRO NACIONAL DE INVESTIGACIONES CARDIOVASCULARES CARLOS III (CNIC), Madrid (ES)

( * ) Notice: Subject to any disclaimer, the term of this patent is extended or adjusted under 35 U.S.C. 154(b) by 102 days.

(21) Appl. No.: 15/523,701

(22) PCT Filed: Oct. 1, 2015

(86) PCT No.: PCT/EP2015/072756
§ 371 (c)(1),
(2) Date: May 2, 2017

(87) PCT Pub. No.: WO2016/071054
PCT Pub. Date: May 12, 2016

(65) Prior Publication Data
US 2017/0328974 A1    Nov. 16, 2017

(30) Foreign Application Priority Data

Nov. 7, 2014    (EP) .................................. 14192290

(51) Int. Cl.
*G01V 3/00*    (2006.01)
*G01R 33/561*    (2006.01)
(Continued)

(52) U.S. Cl.
CPC .......... *G01R 33/5611* (2013.01); *A61B 5/055* (2013.01); *G01R 33/563* (2013.01);
(Continued)

(58) Field of Classification Search
CPC ............ G01R 33/5611; G01R 33/5616; G01R 33/5619; G01R 33/56308; G01R 33/34;
(Continued)

(56) References Cited

U.S. PATENT DOCUMENTS

| 5,653,233 A | 8/1997 | Pelc et al. |
| 6,353,752 B1 | 3/2002 | Madore et al. |

(Continued)

OTHER PUBLICATIONS

Hamilton LH, Fabregat JA, Moratal D, Ramamurthy S, Lerakis S, Parks WJ, Sallee D, Brummer ME. "PINOT": time-esolved parallel magnetic resonance imaging with a reduced dynamic field of view. Magn. Reson. Med. 2011;65:1062-74.

(Continued)

*Primary Examiner* — Rodney E Fuller

(57) ABSTRACT

MR images (10, 20) of an object in its environment within a region of interest are generated. The object executes motion including a plurality of moving phases within a period of time. The method includes the steps of: generating a first image (10) of a region of interest from the first dataset (S2); identifying a dynamic region (12) and a static region (14) inside the first image (10) (S3); editing the first image (10) by masking out the dynamic region (14) (S4); perform- (Continued)

ing an inverse Fourier transformation of the edited first image (16) showing the remaining static region (14) (S5); subtracting the inverse Fourier transformation of the edited first image (16) with the remaining static region (14) from a second dataset (S7) pertaining to one of the moving phases of the object (S6); performing a Fourier transformation on the subtracted second dataset (18) (S8); and generating a second image (20) of a reduced region of interest with respect to the region of interest of the first image (10), which reduced region of interest includes the dynamic region (12) (S9).

13 Claims, 1 Drawing Sheet

(51) Int. Cl.
  *A61B 5/055* (2006.01)
  *G01R 33/563* (2006.01)
  *G06F 17/14* (2006.01)
(52) U.S. Cl.
  CPC ....... *G01R 33/56325* (2013.01); *G06F 17/14* (2013.01); *A61B 2576/023* (2013.01); *G01R 33/5619* (2013.01)
(58) Field of Classification Search
  CPC .............. G01R 33/385; G01R 33/4824; G01R 33/4836; G01R 33/543; G01R 33/5602; G01R 33/561; G01R 33/56554; G06T 11/003
  USPC ........................................................ 324/309
  See application file for complete search history.

(56) References Cited

U.S. PATENT DOCUMENTS

| 7,202,663 | B2 | 4/2007 | Huang | |
| 2005/0100202 | A1* | 5/2005 | Huang | G01R 33/5611 |
| | | | | 382/128 |
| 2008/0292167 | A1* | 11/2008 | Todd | G01R 33/4804 |
| | | | | 382/131 |
| 2014/0303480 | A1 | 10/2014 | Lai | |
| 2014/0376794 | A1* | 12/2014 | Dumoulin | G01R 33/5611 |
| | | | | 382/131 |
| 2016/0097831 | A1* | 4/2016 | Dannels | G01R 33/5611 |
| | | | | 324/318 |
| 2016/0307301 | A1* | 10/2016 | Zhou | G01R 33/4836 |

OTHER PUBLICATIONS

Brummer et al "Noquist: Reduced Field of View Imaging by Direct Fourier Inversion" Magnetic Resonance in Med. 51, p. 331-342—(2004).

Huang et al "Reconstruction with Prior Information for Dynamic MRI" Proc. Intl. Soc. Mag. Reson. Med. 11 p. 2680 (2004).

Lai et al "Improved Cardiac Cine MRI on 3T Using 2D k-t Accelerated Auto-Calibrating Parallel Imaging" Journal of Cardiovascular Magnetic Resonance (2014).

\* cited by examiner

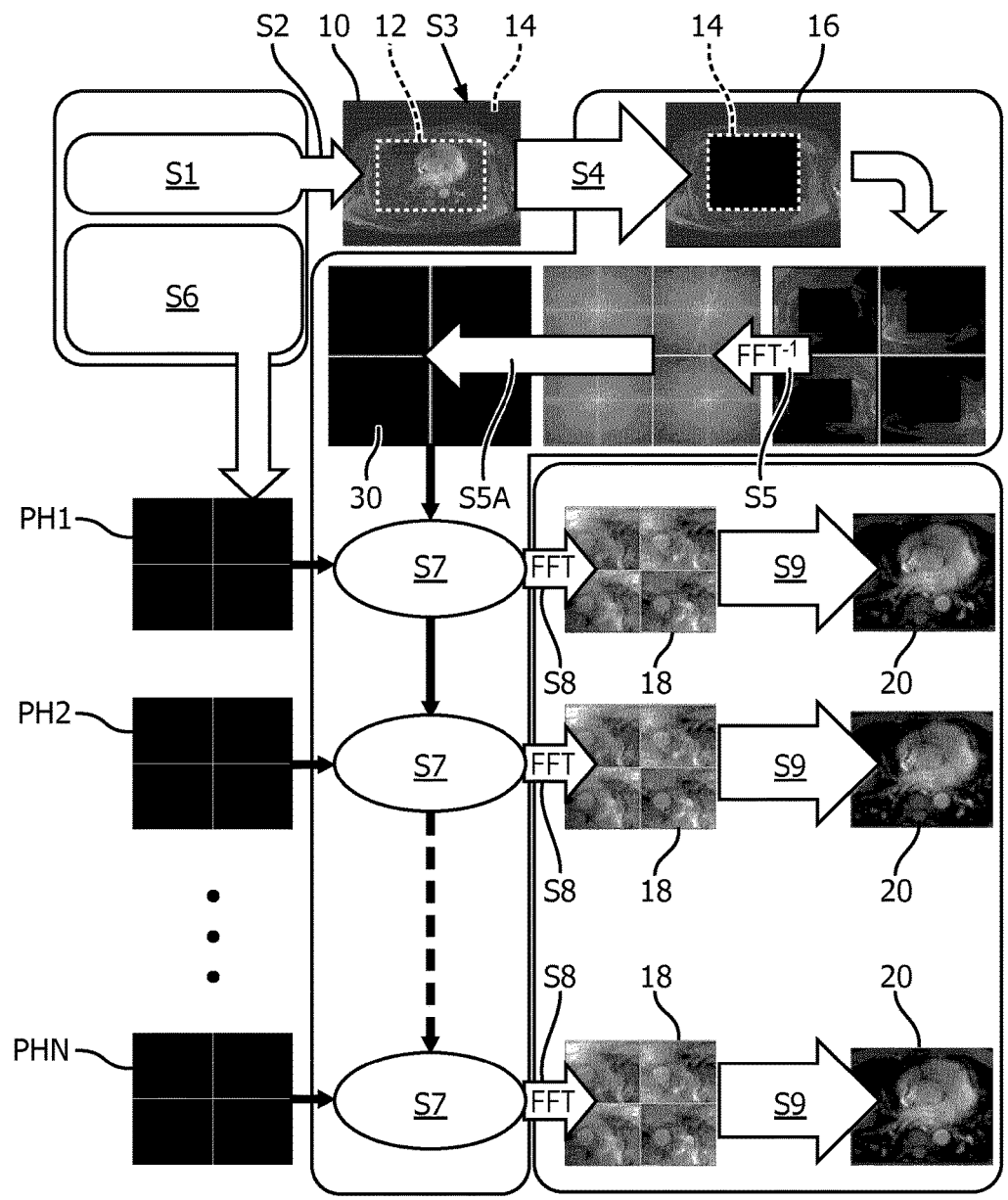

METHOD AND SYSTEM FOR GENERATING MR IMAGES OF A MOVING OBJECT IN ITS ENVIRONMENT

CROSS REFERENCE TO RELATED APPLICATIONS

This application is a U.S. national phase application of International Application No. PCT/EP2015/072756, filed on Oct. 1, 2015, which claims the benefit of EP Application Serial No. 14192290.6 filed on Nov. 7, 2014 and is incorporated herein by reference.

FIELD OF THE INVENTION

The invention relates to the field of generating MR images (MR: Magnetic Resonance) of a moving object, said object executing motion comprising a plurality of moving phases (movement phases) within a period of time. The invention further relates to a corresponding MRI system for generating MR images of an object, said object executing motion comprising a plurality of moving phases within a period of time.

BACKGROUND OF THE INVENTION

There are two limiting factors which reduce the applicability of cardiac MRI (CMRI). The first one is that CMRI examination requires too much scanner time to be performed and many dummy planning scans before the relevant information is acquired. The second one is the high training degree required from technicians to be able to perform cardiac examinations with the right cardiac orientations, making difficult to be spread in any environment. Volumetric 3D isotropic acquisition covering the whole chest could help to avoid these two limitations and improving the cardiac examination workflow.

The scientific paper »L. H. Hamilton et al.: "Time-Resolved parallel Imaging with reduced Dynamic Field of View"; Magn. Reson. Med. 2011; 65:1062-74.<<describes a method named "Parallel Imaging and Noquist in Tandem" (PINOT) for accelerated dynamic image acquisition for cardial MRI (CMRI). This method combines the SPACE-RIP implementation of parallel imaging with the Noquist reduced field of view (rFOV) imaging method, which both use a direct inversion model for image reconstruction.

In PINOT reconstruction it is required to solve a linear system equation like $$\begin{bmatrix} \begin{pmatrix} (k_{t_0,s_0}) \\ (k_{t_0,s_1}) \\ \vdots \\ (k_{t_0,s_{C-1}}) \end{pmatrix} \\ \begin{pmatrix} (k_{t_1,s_0}) \\ (k_{t_1,s_1}) \\ \vdots \\ (k_{t_1,s_{C-1}}) \end{pmatrix} \\ \vdots \\ \begin{pmatrix} (k_{t_N,s_0}) \\ (k_{t_N,s_1}) \\ \vdots \\ (k_{t_N,s_{C-1}}) \end{pmatrix} \end{bmatrix} = \begin{bmatrix} M_S S_0 & M_D S_0 & 0 & \dots & 0 \\ M_S S_1 & M_D S_1 & 0 & \dots & 0 \\ \vdots & \vdots & \vdots & \vdots & \vdots \\ M_S S_{C-1} & M_D S_{C-1} & 0 & \dots & 0 \\ M_S S_0 & 0 & M_D S_0 & \dots & 0 \\ \vdots & \vdots & \vdots & \vdots & \vdots \\ M_S S_{C-1} & 0 & M_D S_{C-1} & \dots & 0 \\ \vdots & \vdots & \vdots & \vdots & \vdots \\ M_S S_0 & 0 & 0 & \dots & M_D S_0 \\ \vdots & \vdots & \vdots & \vdots & \vdots \\ M_S S_{c-1} & 0 & 0 & \dots & M_D S_{C-1} \end{bmatrix} \quad (1)$$

$$\begin{bmatrix} (I_S) \\ (I_{D,t_0}) \\ (I_{D,t_1}) \\ \vdots \\ (I_{D,t_N}) \end{bmatrix},$$

to be able to do the image reconstruction, wherein $S_0, \ldots, S_{C-1}$ represent the sensitivity maps, Ms represents the Fourier transform from those regions that fill the static FoV and $M_D$ represents the Fourier transform from those regions that are updated for every time positioning. In case of 3D cardiac MR images the size of this system matrix becomes difficult to manage and the system inversion to produce image reconstruction is extremely CPU-intensive.

US2014/0303480 describes a method of processing signals from an accelerated MRI scan of a dynamic event occurring in the body of a human patient. The patient is subjected to an MRI examination which includes the relevant portion of his body. Those voxels for which there is no substantially no change over time of the scan are identified and subtracted from the overall scan signal.

SUMMARY OF THE INVENTION

It is an object of the invention to provide a method and a system to overcome the above mentioned limitations.

According to various embodiments of the invention, the method for generating the MR images of the object comprises the steps of:

providing a first dataset pertaining to one of the moving phases of the object;

generating a first image of a region of interest (ROI) from the first dataset;

identifying a dynamic region and a static region inside the first image, wherein said regions are predominantly dynamic or static respectively within the period of time;

editing the first image by masking out the dynamic region;

performing an inverse Fourier transformation of the edited first image showing the remaining static region;

providing a second dataset pertaining to one of the moving phases of the object;

subtracting the inverse Fourier transformation of the remaining static region from the second dataset;

performing a Fourier transformation on the subtracted second dataset; and generating a second image of a reduced region of interest with respect to the region of interest of the first image, which reduced region of interest includes the dynamic region.

Preferably, the identification is performed by manually selecting the static and dynamic region on the first image. For example a box around the heart could be selected as the dynamic region and thereby the region outside the box will be selected as the static region.

As already mentioned, said moving object executes a motion comprising the plurality of moving phases within the total period of time. The data of the provided first and second dataset are previously acquired by data acquisition using an MRI scanner. For subtracting the inverse Fourier transformation of the remaining static region from the second dataset in step (g), this Fourier transformed image (generated in step (e) and based on the first dataset) is undersampled following the same sampling scheme as the second data set.

The inventional idea is based on providing (previously acquired) data of the moving object in its more or less static environment to exploit data redundancy and high SENSE acceleration factor to reach isotropic resolution. This method uses a new approach to manage the reconstruction problem that 3D acquisition will suppose for the above mentioned PINOT reconstruction. As in the PINOT acquisition it can be distinguished two different data sets. In the first dataset it is acquired those k-space lines that will gather the static and dynamic information. In the second dataset a subgroup of k-space lines are acquired for every moving phase (movement phase) of the object based on the idea that it can be recovered some information from the full data set to be able to do the final reconstruction. In this approach—as a difference with PINOT—it is not necessary to build the whole matrix formulation as described in eq. (1).

According to a preferred embodiment of the invention all images or at least the second image is/are generated by use of a SENSE reconstruction. In the SENSitivity Encoding (SENSE) approach, an array of multiple simultaneously operated receiver coils is used for signal acquisition. The array elements are usually surface coils, which exhibit strongly inhomogeneous, mutually distinct spatial sensitivity. The underlying principle of the SENSE approach is to regard the influence of coil sensitivity as an encoding effect similar to gradient encoding. In fact, the sensitivity effect is mathematically largely analogous to gradient encoding. However, a key advantage over the gradient concept is that the sensitivity mechanism permits simultaneous encoding with the multiple distinct sensitivities of the receiver array. Thus, considerable savings in scan time can be achieved by partially replacing sequential gradient switching with parallel sensitivity encoding.

Sensitivity encoding is based on the fact that receiver sensitivity generally has an encoding effect complementary to Fourier preparation by linear field gradients. Thus, by using multiple receiver coils in parallel scan time in Fourier imaging can be considerably reduced. The problem of image reconstruction from sensitivity encoded data is formulated in a general fashion and solved for arbitrary coil configurations and k-space sampling patterns.

According to another preferred embodiment of the invention the moving object is a heart; the MR image is a cardiac MR image; and the moving phases of the object are cardiac phases from a cardiac region. The moving object in its more or less static environment is the whole chest with a non-angulated coronal volume to exploit data redundancy and high SENSE acceleration factor to reach isotropic resolution in cardiac cine images in a single breath-hold. This acquisition and reconstruction methodology allows to obtain 3D isotropic cardiac images in a breath-hold duration with a reconstruction time of minutes.

According to yet another preferred embodiment of the invention at least one further image is generated by repeating steps (f) to (i) of the nine steps (a-i) respectively often. These other images relate to further moving phases (movement phases) PH2 to PHN.

Preferably, the first image is generated by use of a full sampling image and the second image (and all other following images) is/are preferably generated by use of a SENSE reconstruction.

According to another preferred embodiment of the invention the data provided in the first dataset and the second dataset are generated by data acquisition using a MRI scanning unit (MRI scanner). Preferably, the region of interest (ROI) is determined by the Field of View (FoV) of the MRI scanning unit. Accordingly, the reduced region of interest is referred to as a reduced Field of View (rFoV).

Preferably, a plurality of receiver coils are used for said data acquisition. Preferably, the edited first image is divided into a plurality of images, each image inverse Fourier transformed in the k-space domain. The Fourier transformed images for each coil are under-sampled following the same sampling scheme as the sampling of the second data set.

According to another preferred embodiment of the invention, each image of the plurality of images is weighted by a coil sensitivity of the corresponding receiver coil out of the receiver coils before performing the inverse Fourier transformation.

According to various embodiments of the invention, the MRI system for generating MR images of an object is established for performing the following steps:

providing a first dataset pertaining to one of the moving phases of the object;

generating a first image of a region of interest from the first dataset;

identifying a dynamic region and a static region inside the first image, wherein the regions are predominantly dynamic or static respectively within the period of time;

editing the first image by masking out the dynamic region;

performing an inverse Fourier transformation of the edited first image showing the remaining static region;

providing a second dataset pertaining to one of the moving phases of the object;

subtraction of the inverse Fourier transformation of the edited first image with the remaining static region from the second dataset;

performing a Fourier transformation on the subtracted second dataset; and generating a second image of a reduced region of interest with respect to the ROI of the first image, which reduced region of interest includes the dynamic region.

The moving object executes a motion comprising the plurality of moving phases within the period of time, wherein this period of time is a total acquisition time.

According to a preferred embodiment of the invention the system is established for performing the above mentioned method for generating a MR image of a moving object in its environment, especially a heart in the chest.

According to another preferred embodiment of the invention the MRI system comprises (i) a MRI scanning unit for data recording comprising an array of multiple simultaneously operated receiver coils and (ii) a computer based data processing unit for image acquisition of magnetic resonance imaging. The steps (a) to (i) are performed by the data processing unit of the MRI system. The data acquisition steps leading to the steps (a) and (f) are performed by use of the MRI Scanning unit.

Various other embodiments of the invention concern to a computer program product to execute the aforementioned method, especially by use of the aforementioned MRI system.

BRIEF DESCRIPTION OF THE DRAWINGS

These and other aspects of the invention will be apparent from and elucidated with reference to the embodiments described hereinafter.

In the drawings:

FIG. 1 shows a graphic illustration of a procedure for displaying of generating cardiac MR images according to a preferred embodiment of the invention.

DETAILED DESCRIPTION OF EMBODIMENTS

In the following discussion reference is made to the heart as the object to be imaged. The invention is however applicable to other objects like other organs as well. The heart is selected merely as an example.

FIG. 1 shows a schematic representation of all the reconstruction steps using the static information and SENSE acquisition at the same time. This schematic representation represents a procedure for generating cardiac MR (CMR) images 10, 20 of the chest with a non-angulated coronal volume within a ROI and within a total period of time.

The procedure comprises the steps of:

Step 1 (S1): Providing a first dataset of a (first) cardiac phase from a cardiac region;

Step 2 (S2): Generating a first image 10 of a ROI from the first dataset; Step 3 (S3): Identifying a dynamic region 12 and a static region 14 inside the first image 10, wherein these regions 12, 14 are predominantly dynamic or static respectively within the total period of time (S3);

Step 4 (S4): Editing the first image 10 by masking out the dynamic region 12;

Step 5 (S5): Performing an inverse Fourier transformation (FFT−1) of the edited first image 16 showing the remaining static region 14;

Step 6 (S6): Providing a second dataset pertaining to a (second) cardiac phase from the cardiac region S6;

Step 7 (S7): Subtraction of the inverse Fourier transformation (FFT$^{-1}$) of the edited first image 16 with the remaining static region 14 from the second dataset;

Step 8 (S8): Performing a Fourier transformation (FFT) on the subtracted second dataset 18; and Step 9 (S9): Generating a second image 20 of a reduced region of interest (rROI) at least including the dynamic region 12.

Preferably, the identification is performed by manually selecting the static and dynamic region on the first image. For example a box around the heart could be selected as the dynamic region and thereby the region outside the box will be selected as the static region.

The data of the provided first and second dataset are previously acquired by data acquisition. The above mentioned total period of time is a total acquisition time. In preparation of Step 1 (S1), e.g. a full FoV single acquisition is performed to remove folds over artifacts. In Preparation of Step 6 (S6) an undersampling acquisition of the ky-kz space is performed for updating the reduced FoV (rFoV) for every cardiac phase. The term full FoV corresponds to the (complete) ROI and the term rFoV corresponds to the reduced ROI.

Those skilled in the art will understand in cases that the second dataset (rFoV) is undersampled compared to the first dataset, preferably also a Step 5a is applied between Step 5 and Step 7. In Step 5a, the inverse Fourier transformation (FFT$^{-1}$) of the edited first image 16 will be undersampled in the same way as the undersampling used when providing (acquiring) the second dataset. So the procedure comprises the following steps: Step 1

(S1): Acquiring a first dataset of a (first) cardiac phase from a cardiac region;

Step 2 (S2): Generating a first image 10 of a ROI from the first dataset;

Step 3 (S3): Identifying a dynamic region 12 and a static region 14 inside the first image 10, wherein these regions 12, 14 are predominantly dynamic or static respectively within the total period of time (S3);

Step 4 (S4): Editing the first image 10 by masking out the dynamic region 12;

Step 5 (S5): Performing an inverse Fourier transformation (FFT−1) of the edited first image 16 showing the remaining static region 14;

Step 5a (S5a): Undersampling the inverse Fourier transformation (FFT−1) of the edited first image 16 using a undersampling strategy and thereby providing an undersampled first dataset 30

Step 6 (S6): Acquiring a second dataset pertaining to a (second) cardiac phase from the cardiac region S6, wherein the second dataset is undersampled compared to the first dataset by using the undersampling strategy during acquisition of the second dataset;

Step 7 (S7): Subtraction of the undersampled first dataset 30 from the second dataset;

Step 8 (S8): Performing a Fourier transformation (FFT) on the subtracted second dataset 18; and Step 9 (S9): Generating a second image 20 of a reduced region of interest (rROI) at least including the dynamic region 12.

As in the PINOT acquisition, the depicted procedure can distinguish two different data sets. In the first data set it is acquired those k-space lines that will gather the static and dynamic information. In the second data set a subgroup of k-space lines are acquired for every cardiac phase (heart phase) base on the idea that it can be recovered some information from the full data set to be able to do the final reconstruction. In the approach—as a difference with PINOT—it is not necessary to build the whole matrix formulation as is described in Eq. (1). In contrast the reconstruction is spitted in three different stages.

1st Stage: In this reconstruction stage a full image 10 is generated for a single cardiac phase using the first data set described above (S2). This image 10 can be generated using conventional SENSE reconstruction or full sampling image to improve signal accuracy.

2nd Stage: In this reconstruction stage in the full reconstructed image the previously defined dynamic region is set to 0 (S4) in order to get the information just from those static regions 14 that remain equal along all cardiac phases. In this reconstruction stage the images 16 are weighted by coil sensitivities of each coils and inverse Fourier transformed in the k-space domain (S5). The Fourier transformed images for each coil are under-sampled following the same sampling scheme as the second data set described above (indicated by the unlabeled arrow between S5 and S7). Finally, the generated k-space lines from the static region are subtracted from the updated k-space lines in every cardiac phase (S7).

3rd Stage: In this reconstruction stage the images generated in the 2nd stage are Fourier transformed into the image space (S8) and reconstructed using conventional SENSE reconstruction but just taken the information from the reduced FoV (S9).

Following this approach the SENSE reconstruction and the NoQUIST-like reconstruction are much separated. SENSE information is just used in the third stage while the NoQUIST-like information is just used in the second stage of the reconstruction. Moreover, in the third stage of the reconstruction just a reduced region is reconstructed improving the reconstruction speed compared to conventional SENSE reconstruction for 3D cases.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The work leading to this invention has received funding from the European Union Seventh Framework Programme (FP-7-HEALTH-2009) under grant agreement number 242038.

The invention claimed is:

1. A method for generating magnetic resonance (MR) images of an object, said object executing motion comprising a plurality of moving phases within a period of time, the method comprising the steps of:
   (a) acquiring a first dataset in k-space by using a plurality of receiver coils pertaining to the object using a SENSE undersampling scheme;
   (b) reconstructing a first image in image space of a region of interest from the first dataset by means of SENSE reconstruction;
   (c) identifying a dynamic region and a static region inside the first image in image space, wherein said regions are predominantly dynamic or static respectively within the period of time;
   (d) editing the first image in image space by masking out the dynamic region;
   (e) weighing the edited first image by coil sensitivities of multiple MR receive coils;
   (f) performing an inverse Fourier transformation of the edited and weighed first image showing the remaining static region to transform the edited and weighted first image into k-space;
   (g) acquiring a second dataset in k-space pertaining to one of the moving phases of the object by using the multiple MR receive coils, wherein the second dataset is provided by means of undersampling during acquisition, resulting in a reduced field of view (rFoV) compared to a field of view of the first dataset and in addition using the same SENSE undersampling scheme as for the acquisition of the first dataset;
   (h) subtracting in k-space the inverse Fourier transformation of the edited first image with the remaining static region from the second dataset; and
   (i) reconstructing the second dataset with the edited first dataset subtracted out into a second image of a reduced region of interest with respect to the region of interest of the first image by means of SENSE reconstruction, which reduced region of interest includes the dynamic region.

2. The method according to claim 1, wherein at least one further second image is generated by repeating steps (g)-(i).

3. The method according to claim 1, wherein the first image is a fully sampled image.

4. The method according to claim 1, wherein the edited first image is divided into a plurality of sub-images, and further including inverse Fourier transforming each of the plurality of sub-images in the k-space domain.

5. A non-transitory computer-readable medium carrying a computer program which controls a computer processor of a magnetic resonance imaging system to execute the method according to claim 1.

6. A method of magnetic resonance (MR) cardiac imaging for generating a plurality of cardiac MR images of a patient in each of a plurality of cardiac phases, the method comprising:
   acquiring a plurality of k-space datasets of a chest region of a patient using SENSE undersampling, each of the plurality of k-space datasets being in one of the plurality of cardiac phases;
   reconstructing a chest image using one of the plurality of k-space datasets using SENSE reconstruction, the chest image including a dynamic region depicting the patient's heart and a static region depicting portions of the patient chest around the patient's heart;
   transforming the static region of the chest image into k-space to generate a static region k-space dataset;
   subtracting the static region k-space dataset from each of the plurality of k-space datasets;
   reconstructing a plurality of heart images including a heart image in each of the plurality of cardiac phases by reconstructing using SENSE reconstruction a reduced field of view of each of the plurality of k-space datasets with the static region k-space dataset subtracted out from k-space into one of the plurality of cardiac images.

7. The method of MR cardiac imaging according to claim 6, further including:
   before transforming the static region of the chest image into k-space, weighting the static region of the chest image by coil sensitivities of multiple MR receive coils which acquire the plurality of k-space datasets.

8. The method of MR cardiac imaging according to claim 6, wherein reconstructing the chest image and reconstructing the heart images and transforming the static region of the chest image into k-space each include at least one of Fourier transformation and inverse Fourier transformation.

9. The method of MR cardiac imaging according to claim 6, wherein the plurality of heart images each have a reduced field of view relative to the chest image.

10. The method of MR cardiac imaging according to claim 6, further including:
    displaying the plurality of heart images on a video monitor.

11. A magnetic resonance imaging (MRI) system for generating MR images of an object, said object executing motion comprising a plurality of moving phases within a period of time, the system is established for performing the following steps:
    acquiring a first dataset by using a plurality of receiver coils pertaining to one of the moving phases of the object using a SENSE undersampling scheme;
    reconstructing a first image of a region of interest from the first dataset by means of SENSE reconstruction;
    identifying a dynamic region and a static region inside the first image, wherein said regions are predominantly dynamic or static respectively within the period of time;
    editing the first image by masking out the dynamic region;
    weighing the edited first image by coil sensitivities of the multiple receive coils;
    performing an inverse Fourier transformation of the edited and weighed first image showing the remaining static region;

acquiring a second dataset pertaining to one of the moving phases of the object by using the plurality of receiver coils, wherein the second dataset is provided by means of undersampling during acquisition, resulting in a reduced field of view (rFoV) compared to a field of view of the first dataset and in addition using the same SENSE undersampling scheme as for the acquisition of the first dataset;

subtracting the inverse Fourier transformation of the edited first image with the remaining static region from the second dataset;

performing a Fourier transformation on the subtracted second dataset; and generating a second image of a reduced region of interest with respect to the region of interest of the first image, which reduced region of interest includes the dynamic region.

12. The system according to claim 11, wherein the system is established for performing a method for generating magnetic resonance images of an object, said object executing motion comprising a plurality of moving phases within a period of time, the method comprising:

acquiring a first dataset by using a plurality of receiver coils pertaining to one of the moving phases of the object using a SENSE undersampling scheme;

reconstructing a first image of a region of interest from the first dataset by means of SENSE reconstruction;

identifying a dynamic region and a static region inside the first image, wherein said regions are predominantly dynamic or static respectively within the period of time;

editing the first image by masking out the dynamic region;

weighing the edited first image by coil sensitivities of the multiple receive coils;

performing an inverse Fourier transformation of the edited and weighed first image showing the remaining static region;

acquiring a second dataset pertaining to one of the moving phases of the object by using the plurality of receive coils, wherein the second dataset is provided by means of undersampling during acquisition, resulting in a reduced field of view (rFoV) compared to a field of view of the first dataset and in addition using the same SENSE undersampling scheme as for the acquisition of the first dataset;

subtracting the inverse Fourier transformation of the edited first image with the remaining static region from the second dataset;

performing a Fourier transformation on the subtracted second dataset; and generating a second image of a reduced region of interest with respect to the region of interest of the first image, which reduced region of interest includes the dynamic region.

13. The system according to claim 11, comprising a computer based data processing unit for image generation of magnetic resonance images.

* * * * *